(12) United States Patent
Rassman et al.

(10) Patent No.: US 8,317,804 B1
(45) Date of Patent: Nov. 27, 2012

(54) HAIR HARVESTING APPARATUS

(75) Inventors: William Rassman, Los Angeles, CA (US); Jae P. Pak, Los Angeles, CA (US)

(73) Assignee: William Rassman, Los Angeles, CA (US)

( * ) Notice: Subject to any disclaimer, the term of this patent is extended or adjusted under 35 U.S.C. 154(b) by 112 days.

(21) Appl. No.: 12/780,834

(22) Filed: May 14, 2010

Related U.S. Application Data

(62) Division of application No. 11/531,862, filed on Sep. 14, 2006, now abandoned.

(51) Int. Cl.
*A61B 17/50* (2006.01)
(52) U.S. Cl. ............................................. 606/133
(58) Field of Classification Search .......... 606/131, 606/133, 167, 169, 179, 180, 184, 187; 604/19, 604/22; 600/204, 407, 562–567; 83/53, 83/177
See application file for complete search history.

(56) References Cited

U.S. PATENT DOCUMENTS

| | | | |
|---|---|---|---|
| 4,785,826 A | 11/1988 | Ward | |
| 4,898,574 A * | 2/1990 | Uchiyama et al. | 604/22 |
| 5,205,816 A * | 4/1993 | Dodson et al. | 604/1 |
| 5,339,799 A | 8/1994 | Kami et al. | |
| 5,464,389 A * | 11/1995 | Stahl | 604/22 |
| 5,628,743 A | 5/1997 | Cimino | |
| 5,782,851 A | 7/1998 | Rassman | |
| 5,827,297 A * | 10/1998 | Boudjema | 606/133 |
| 6,168,590 B1 | 1/2001 | Neev | |
| 6,200,326 B1 | 3/2001 | Narayanan et al. | |
| 6,572,625 B1 * | 6/2003 | Rassman | 606/133 |
| 6,585,746 B2 | 7/2003 | Gildenberg | |
| 6,589,201 B1 * | 7/2003 | Sussman et al. | 604/27 |
| 6,689,086 B1 | 2/2004 | Nita et al. | |
| 7,130,717 B2 * | 10/2006 | Gildenberg | 700/245 |
| 7,156,856 B2 * | 1/2007 | Feller | 606/133 |
| 2004/0116942 A1 | 6/2004 | Feller | |
| 2006/0161179 A1 | 7/2006 | Kachenmeister | |
| 2006/0178677 A1 | 8/2006 | Brinson | |
| 2006/0216781 A1 | 9/2006 | Gebing | |
| 2007/0106306 A1 * | 5/2007 | Bodduluri et al. | 606/133 |
| 2008/0033455 A1 | 2/2008 | Rassman et al. | |

* cited by examiner

*Primary Examiner* — Ryan Severson
*Assistant Examiner* — David Eastwood
(74) *Attorney, Agent, or Firm* — Lawrence S. Cohen

(57) ABSTRACT

The extraction of a hair graft from a harvesting area of a scalp employs a hollow punch fitted with an auxiliary instrumentation for separating a target graft from collagen fibrils which resist extraction. A water jet which follows the annular path of the punch as it rotates into the scalp is described as well as a vibrating punch alternative embodiment for achieving the desired separation.

4 Claims, 4 Drawing Sheets

HAIR HARVESTING APPARATUS

FIELD OF THE INVENTION

This invention relates to hair harvesting apparatus and more particularly to apparatus for extracting single follicular units from a harvesting area of the skin.

BACKGROUND

Presently, a patch of skin is excised from the rear area of a scalp and the scalp is then sutured. This patch is then dissected under a microscope and hair follicular units are isolated. The process is slow, tedious, exacting and expensive. It would be advantageous to develop a hair graft harvesting technique which would permit the removal of individual hair grafts from a harvesting area of a scalp or hair bearing skin. Not only would such a technique expedite hair graft harvesting and reduce cost, it also would eliminate the surgical procedure of excising a patch of skin and the attending suturing.

But the harvesting of individual hair follicular units or grafts has its own problems:

U.S. Pat. No. 6,572,625 demonstrates a mechanism for alignment of hair follicles within a follicular unit so that the follicular unit can be extracted, one follicular unit (FU) at a time. U.S. Pat. No. 6,572,625 sets up a situation where a hollow punch with a sharp or dull cutting edge can be used to remove the follicular unit with reduced damage of cutting or amputating the follicles in the FU with perfect alignment. When a punch is introduced to surround the FU, the hollow tube gathers the hair follicles as it is advanced deeper into the scalp or hair bearing skin (a distance of about 5-7 mm).

The anatomy of a follicular unit is not cylindrical in its normal undisturbed state, in vivo. The hairs of the FU grow in groups of one, two, threes, and four hairs. The hairs of the FU exit at the skin surface in close proximity to one another. However, the hairs of the FU sometimes diverge and cone out in the dermal and fatty layer beneath the skin. Hairs of the FU have a maximal divergence at the location of the bulb.

The hair follicles are connected to stroma (collagen fibrils) which forms a lattice work of supporting structures, forming a framework holding the hair follicles in place and connecting the hair follicles to the surrounding fat and blood vessels. This fibrous framework is made up of collagen and the nature of the collagen varies from person to person. Some collagen fibrils are elastic and some inelastic. These inherent characteristics of the FU make the extraction of the FU uniquely variable on an individual basis.

In some people, the amount of elastic fibrils is disproportionably high in number, while in other individuals they it is disproportionably low in numbers. During the coring of an FU, it is theorized that if the number of elastic fibrils is high, the hollow punch easily 'gathers' the hair follicles as it is advanced into the deeper fat, probably tearing at the supporting stroma and breaking it apart. In those with a high elastic content, the cutting or breaking of these elastic fibrils occurs easily as the hair follicles advance into the descending hollow punch.

In some people, however, the elastic fibrils are few in number and the inelastic fibrils are high so that the hair and the surrounding structures do not easily cut or tear as the hollow punch is advanced. When this happens, the point of greatest weakness may be the hair shafts and the hair shaft is either cut or torn apart, damaging the FU as attempts are made to remove it.

The extraction of the follicular unit is a mechanical process and it is heavily influenced by mechanical factors related to the stroma that support each and every hair follicle. The results of these anatomical variations make extraction of each hair follicle variable on an individual and even local (different areas of the skin) basis. Variations in successful extraction of hairs within an FU often produce unacceptable variation in the success of FU Extraction.

SUMMARY

The invention is based on the realization that the extraction of individual hair follicular units from a harvest area of the hair bearing skin could be improved by a mechanism which assists an advancing hollow punch as it moves into the hair bearing skin around a target follicular unit. Such an assist is provided by applying vibrational energy to the punch as it advances or by cutting the collagen fibrils about the advancing punch preferably by a water jet scalpel controlled to follow an annular path along the annular distal surface of the punch. In one embodiment, a channel is provided in the wall of the punch. A source of water is coupled to the channel and a pump, under the control of the operator, generates a water jet at the distal surface of the punch. The water jet follows a circular path as the punch rotates upon entry into the skin. A punch with a sharp distal end has been found often to result in the extraction of damaged grafts a consequence which is avoided by a dull punch with an auxiliary instrumentation to separate inelastic collagen fibrils which resist extraction.

DETAILED DESCRIPTION OF ILLUSTRATIVE EMBODIMENTS

Figure 1:
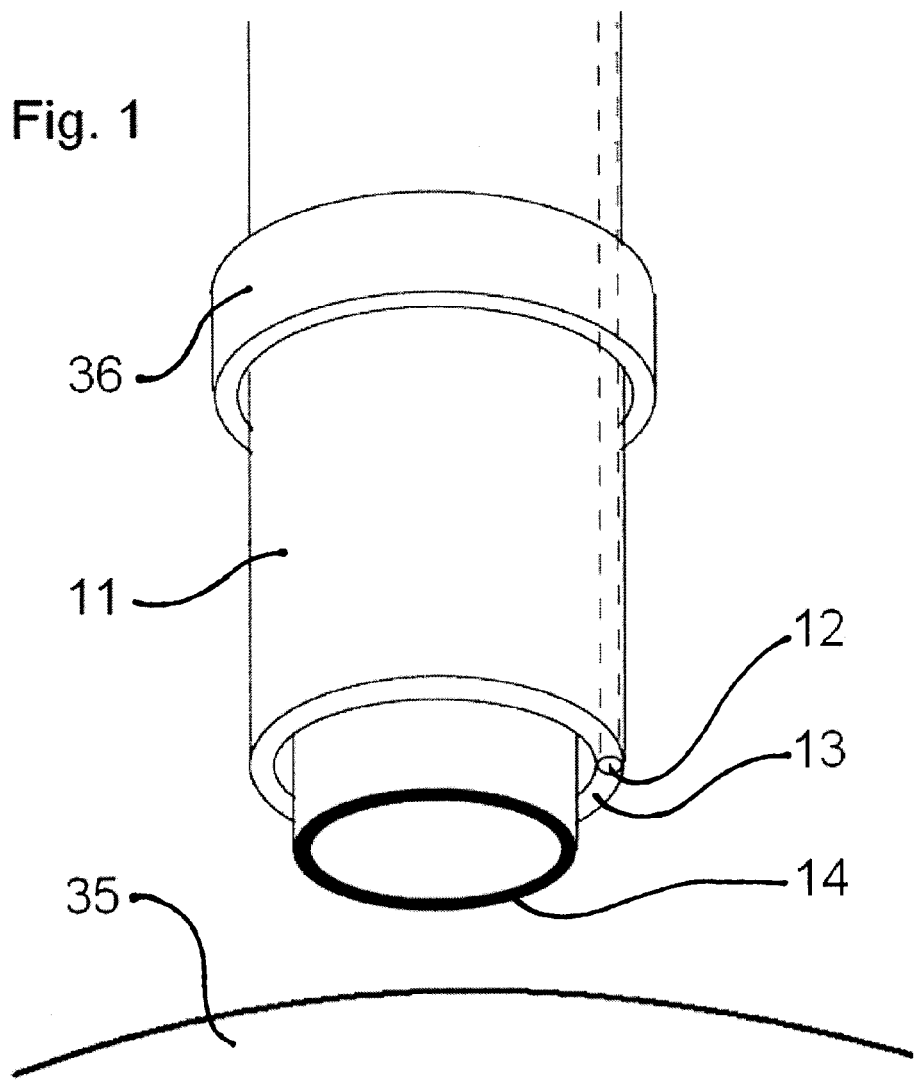
FIG. 1 is a schematic representation of a graft extraction punch in accordance with the principles of this invention.
Figure 2:
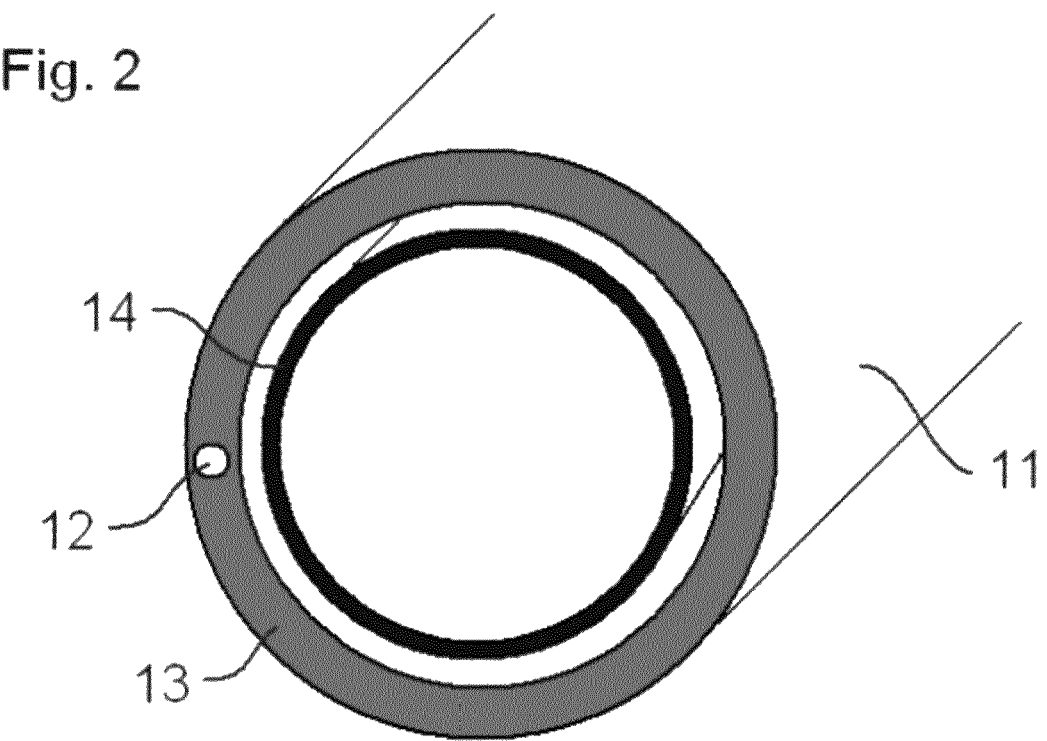
FIG. 2 is an enlarged end view of the punch of FIG. 1.

FIG. 1 is a schematic side view of a punch for extracting hairgrafts from a hair bearing skin in accordance with the principles of this invention. FIG. 2 is an enlarged view of the distal end of the punch of FIG. 1.

Figure 3:
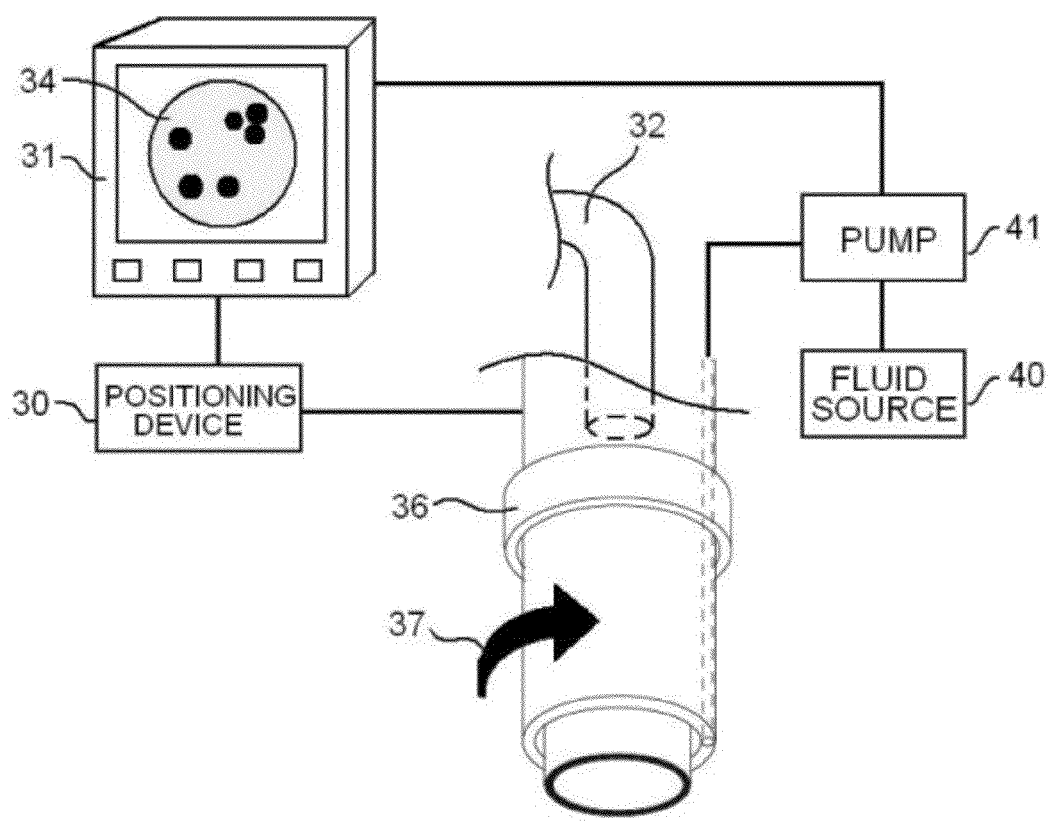
FIG. 3 is a system block diagram for the operation of the punch of FIG. 1.

FIG. 3 is a schematic system diagram of apparatus 10 operative for extracting single follicular unit hair grafts from a hair bearing skin in accordance with the principles of this invention. The apparatus comprises a hollow punch 11 of FIG. 1 with a channel 12 journalled into the wall of the punch exiting at the distal end 13 as shown in FIG. 2.

A second punch 14 is positioned coaxially with respect to the axis of punch 11. Punch 14 has a diameter just larger than the footprint made by the hair of a follicular unit exiting the hair bearing skin. Punch 14 has a sharp distal end and punch 11 has a dull distal end. The punches are free to move individually along the common axis but conveniently are coupled to one another.

Punch 11 is secured to a positioning device 30 for aligning punch 11 with a target hair graft for extraction. The positioning device is operative under the control of a controller which conveniently comprises a computer 31. An imaging device such as an optical fiber 32 is positioned to capture the image of target grafts as is disclosed in U.S. Pat. No. 6,572,625, issued Jun. 3, 2003 and also in co pending patent application Hair Extraction Device and Method for its Use filed Aug. 3, 2006. The image is displayed on monitor 34 of computer 31.

The positioning device is positioned to move punch 11 about the surface of a hair bearing skin 35 as indicated in FIG. 1. An operator observes an image on monitor 34 and selects a target graft. Both punch 11 and Punch 14 are now properly positioned for excising a hair graft. The operator activates the positioning assembly to advance Punch 14 to penetrate or score the skin at the target site. Punch 14 is then withdrawn. The operator then activates the positioning device to move punch 11 into the hair bearing skin and to rotate punch 11 as it advances. The advance of the punch may be controlled to be limited to a depth of approximately 7 mm by the position of a shoulder 36 positioned to abut the hair bearing skin surface when the maximum penetration is reached. The rotation of the advancing punch is indicated by curved arrow 37 in FIG. 3. This rotation may be cycled or oscillated in the clockwise and counter-clockwise direction for optimal effect, conveniently controlled by the controller (31).

Channel 12 in punch 11 is connected to fluid source 40 to supply fluid to the channel. The pressure, pulse frequency and pulse duration are determined by pump 41 also conveniently controlled by the controller (31). The number of rotations or oscillations of the punch also is controlled by the controller. The diameter of the punch is selected to be slightly larger than a follicular unit which is approximately 0.7 mm and the diameter of the channel 12 typically range 120 microns or less In operation, an advancing punch (11) with micro water jet stream under a pressure of up/to (but not limited to) 150 bar with or without pulsations rotating along the perimeter of the punch may be sufficient to achieve successful dissection and extraction of the most resistant grafts in a single rotation.

The punch, with an inner diameter of approximately 0.8 mm to 1.0 mm, typically has a dull distal end but it may also have a sharp cutting edge. In either case, a micro water jet increases the success rate of undamaged graft extraction.

The fluid employed may be normal saline water. But other fluids such as lactated ringers solution may be used.

Figure 4:
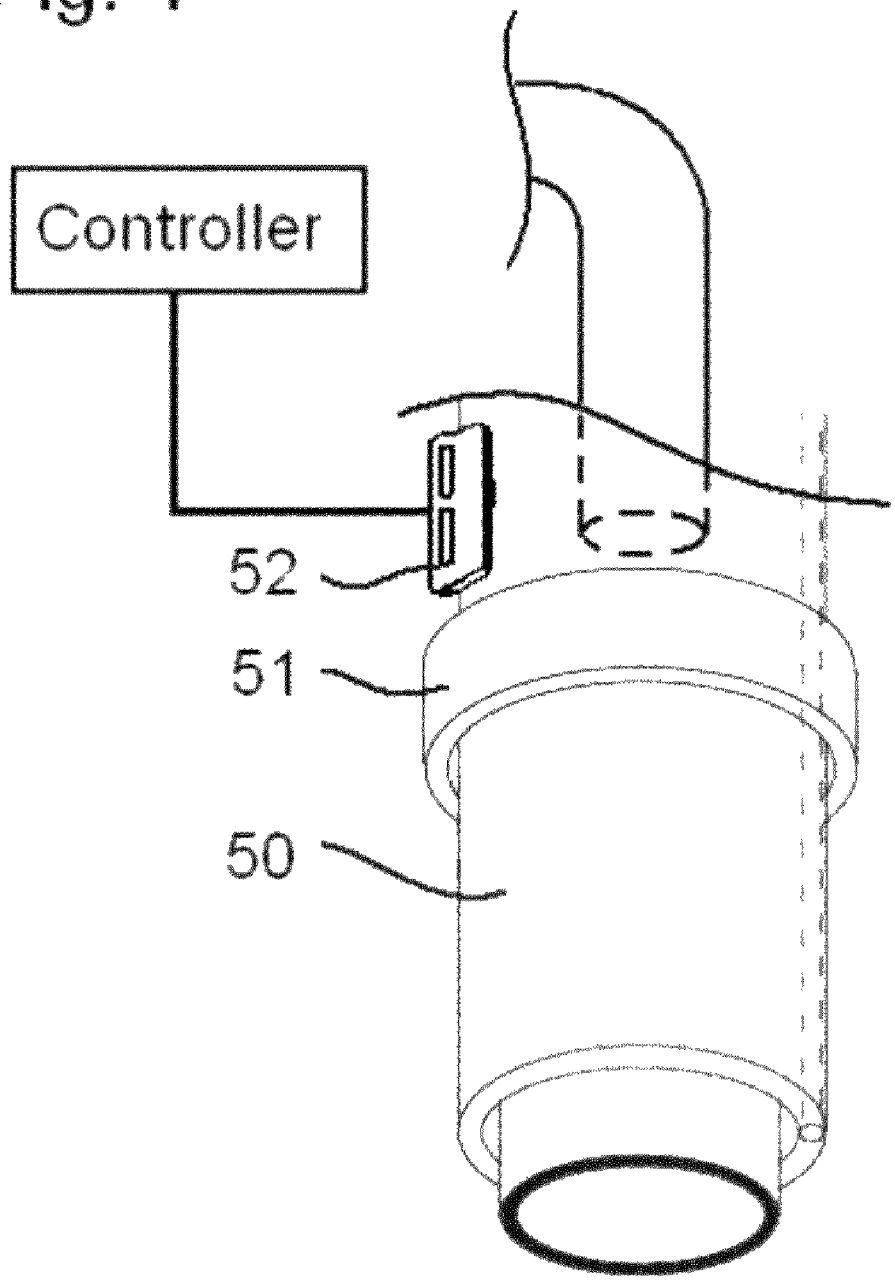
FIG. 4 is a schematic representation of an alternative graft extraction punch in accordance with the principles of this invention.

FIG. 4 shows an alternative embodiment where a vibratory device is attached to a punch and activated as the punch is (rotationally) advanced about a target follicular unit. Specifically, FIG. 4 shows a punch 50 illustratively with a shoulder 51 with a transducer 52 coupled to the punch. In the embodiment of FIG. 4, the transducer is activated when an operator activates a positioning assembly for advancing the punch into the hair bearing skin at a target graft. The vibration of the punch produces successful extraction of undamaged grafts and may be implemented by an ultrasonic micro-vibration device such as those used in electric tooth brushes or those used in dental offices.

In an embodiment where a hollow punch with a sharp distal end is positioned within hollow punch 11 and moveable along the center axis of the punch, controller 31 is adapted to move punch 14 into the scalp or skin in a manner to pierce the skin and to then withdraw the punch. The punch may be fixed to the interior wall of another hollow punch 11 by attachment arms or by a nest of telescoping tubes operative to move punch 14 along the z axis when hollow punch 11 is positioned at a target graft. The telescoping tubes may be operative to move punch 14 along the coaxial path in response to the rotation of the outermost cylinder of the nest. The rotation of the outermost cylinder is produced conveniently by a belt (not shown) coupled to a reversible motor under the control of the controller such as 31 of FIG. 3.

In embodiments where punch 11 has a sharp distal end, punch 14 may not be necessary. In such embodiments punch 11 is rotated or oscillated relatively slowly to allow the fluid jet to cut the soft tissue surrounding a target graft to lesser the damage which typically is caused by the sharp cutting edge.

What has been described herein is merely illustrative of the principles of this invention and various modifications thereof may be generated by those skilled in the art within the spirit and scope of the invention as encompassed by the following claims: For example, the rotation of the punch may be achieved by a worm gear, a belt arrangement, manual rotation, or a mechanical attachment. The shoulder (36) may be adjustable along the coaxial path of the punch and pre-positioned prior or even during a set of extraction procedures. Also, the imaging instrumentation may be implemented by a high power video camera, computer assisted visual system, or direct visualization along with or instead of the optical fiber illustrated.

What is claimed is:

1. A method for extracting a follicular unit of hair from a hair bearing skin, comprising:
   providing a first hollow punch having a distal end with an interior diameter larger than the diameter of the bulb of a follicular unit, and a channel in a wall of said first hollow punch exiting at said distal end for providing an exit for a jet fluid stream at said distal end;
   providing a second hollow punch coaxial with said first hollow punch, said second hollow punch having a sharp distal end;
   aligning said first and second hollow punches with a selected follicular unit; and
   controllably advancing said second hollow punch prior to advancing said first punch in a manner to pierce the skin around the selected follicular unit and then withdrawing said second hollow punch;
   advancing while rotating said first hollow punch responsive to the withdrawal of said second hollow punch into skin surrounding the selected follicular unit;
   providing a jet fluid stream through said channel to operate as a fluid scalpel annularly cutting the anatomical structure surrounding the selected follicular unit as said first hollow punch rotates and advances;
   removing the selected follicular unit.

2. The method of claim 1 further comprising:
   providing a shoulder on the first hollow punch located a selected distance above its distal end; and
   using the shoulder as a limit to the depth of advancement of the first hollow punch.

3. The method of claim 1 further comprising:
   providing a fluid source to supply fluid to the channel to establish the jet stream; and
   controlling the jet stream at a selected pressure either continuous or pulsating.

4. The method of claim 1 wherein the distal end of the first hollow punch is either dull or sharp.

* * * * *